United States Patent
Fattori

(10) Patent No.: US 7,386,904 B2
(45) Date of Patent: Jun. 17, 2008

(54) DRIVE SYSTEM FOR ELECTRIC TOOTHBRUSHES AND THE LIKE

(75) Inventor: Joseph Edward Fattori, Mendham, NJ (US)

(73) Assignee: Colgate-Palmolive Company, New York, NY (US)

( * ) Notice: Subject to any disclaimer, the term of this patent is extended or adjusted under 35 U.S.C. 154(b) by 394 days.

(21) Appl. No.: 10/735,970

(22) Filed: Dec. 15, 2003

(65) Prior Publication Data
US 2005/0125919 A1 Jun. 16, 2005

(51) Int. Cl.
A61C 17/22 (2006.01)
A61C 17/40 (2006.01)
A61C 17/32 (2006.01)

(52) U.S. Cl. .................. 15/22.1; 15/22.4; 15/167.1
(58) Field of Classification Search .......... 15/22.1, 15/22.4, 167.1
See application file for complete search history.

(56) References Cited

U.S. PATENT DOCUMENTS

| | | | |
|---|---|---|---|
| 3,029,651 A | | 4/1962 | Flatt |
| 3,538,530 A | * | 11/1970 | Stemme ............... 15/22.1 |
| 4,149,291 A | | 4/1979 | Stoltz |
| 5,253,382 A | * | 10/1993 | Beny .................. 15/22.1 |
| 5,625,914 A | | 5/1997 | Schwab |
| 5,813,079 A | * | 9/1998 | Halm ................. 15/167.1 |
| 6,895,625 B2 | * | 5/2005 | Lev et al. ............... 15/28 |
| 2003/0066145 A1 | * | 4/2003 | Prineppi ............... 15/22.1 |

FOREIGN PATENT DOCUMENTS

| | | |
|---|---|---|
| DE | 198 02 904 A1 | 7/1999 |
| DE | 101 06 610 A1 | 2/2002 |
| WO | WO 03/024353 | 3/2003 |

OTHER PUBLICATIONS

Merriam-Webster Collegiate Dictionary, Tenth Edition, 1998. "Track".*
Slide. www.dictionary.reference.com/browse/slide. May 3, 2007.*

* cited by examiner

Primary Examiner—Shay L Karls
(74) Attorney, Agent, or Firm—Michael J. Wallace, Jr.

(57) ABSTRACT

A drive system for imparting motion to a treating implement such as a toothbrush or the like includes a cam rotatably driven around an axis of rotation by a motor. The cam has a closed loop cam track eccentric to the axis of rotation. A control member is disposed between the cam and the treating implement head. The control member has a control slot extending completely through the control member. A pivot member is located between the control member and the treating implement head. The drive system further includes a drive shaft with its drive end freely mounted in the cam track. The drive shaft extends through the control slot and through the pivot member with its driven end operatively connected to the drive connection of the implement head. As a result, when the cam member is rotated the direction of movement of the drive shaft is controlled by the drive shaft being confined for sliding movement in the control slot. The drive shaft is still capable of rotating because of its free mounting in the cam track. The torque and the angle of oscillation imparted to the movable treating elements is determined by the location of the pivot member with respect to the treating head.

20 Claims, 3 Drawing Sheets

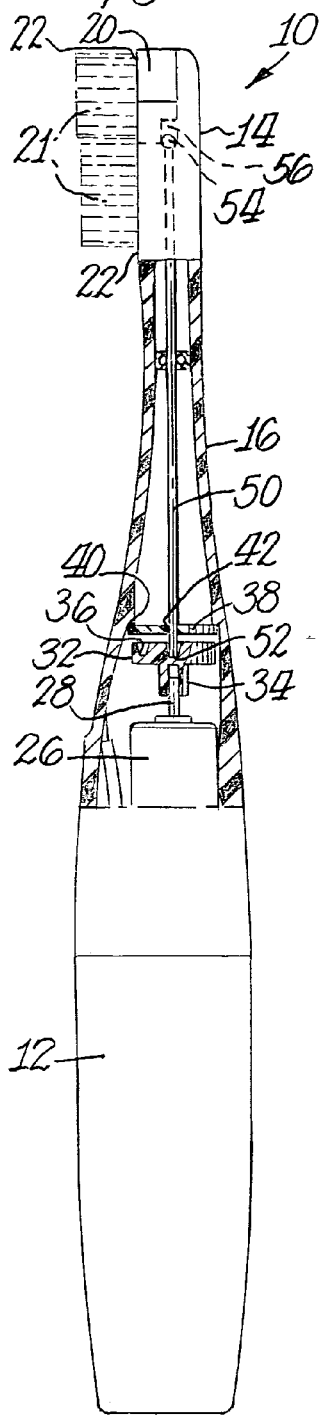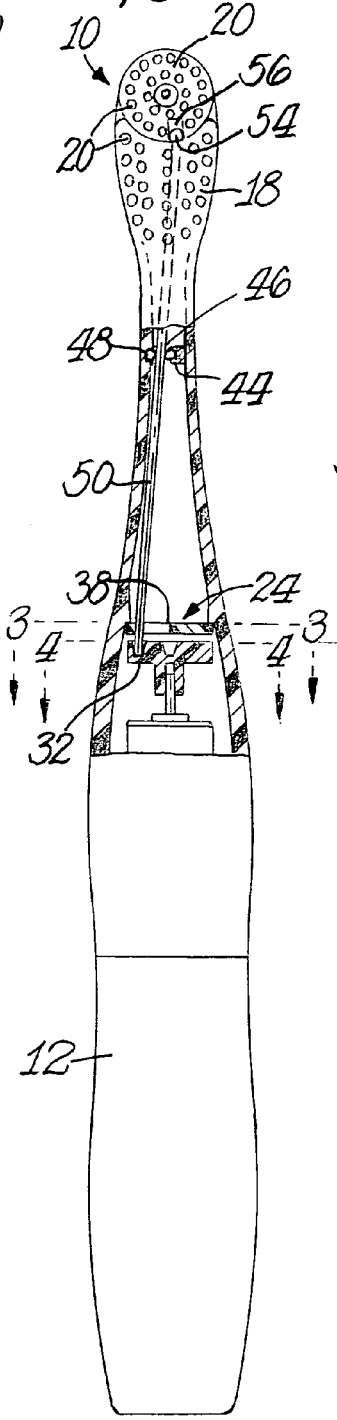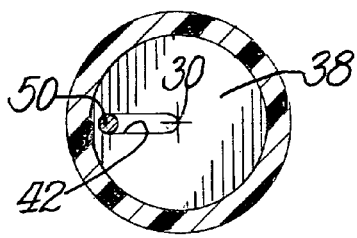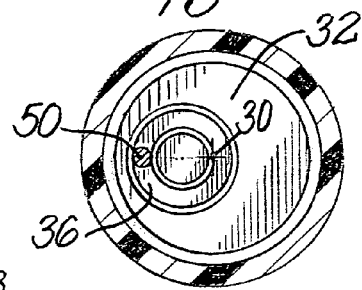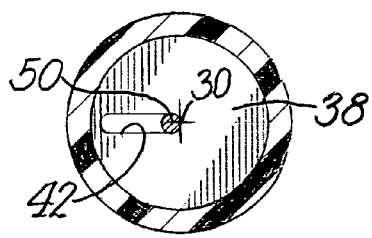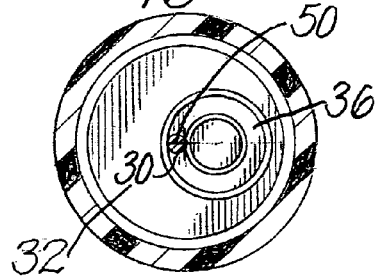

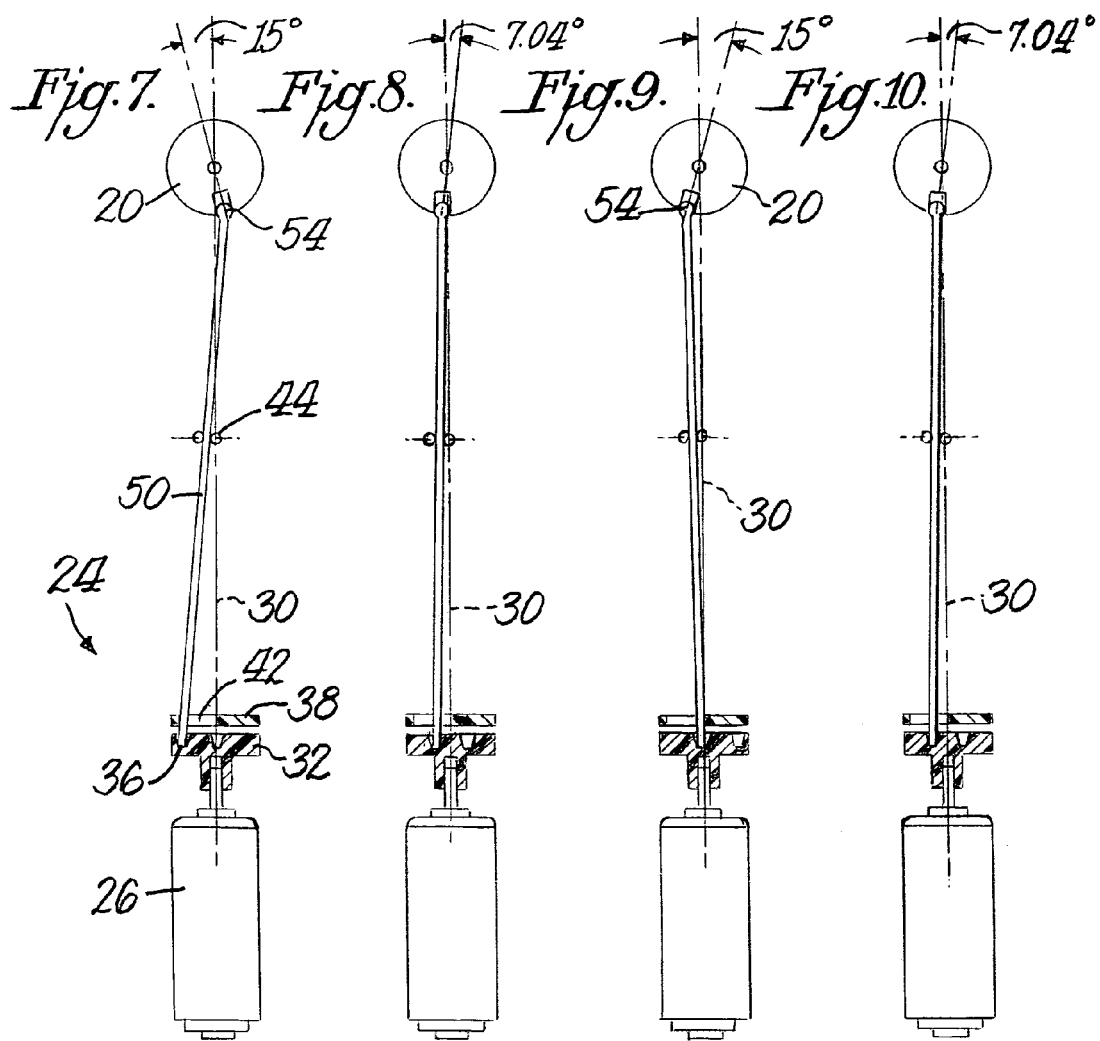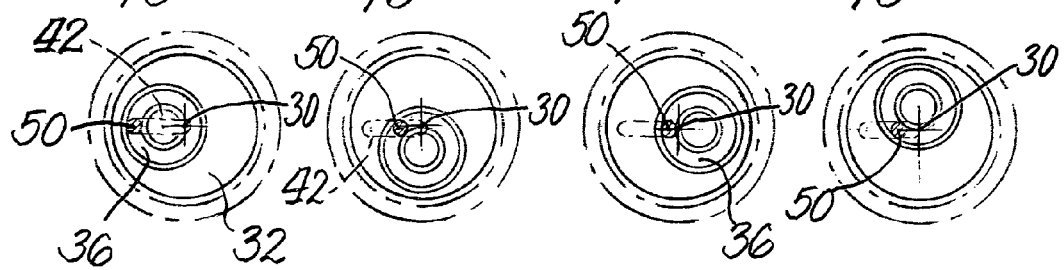

DRIVE SYSTEM FOR ELECTRIC TOOTHBRUSHES AND THE LIKE

BACKGROUND OF THE INVENTION

Various treating implements exist which include movable treating elements on the head portion of the implement. For example, power toothbrushes frequently have a brush head connected to the handle wherein at least a portion of the brush head rotates continuously in one direction or oscillates back and forth. Other treating implements which may have movable treating elements include, for example, electric razors, clippers, massage devices and various other personal grooming devices.

An example of a power operated toothbrush having an oscillating disk on its cleaning head is found in WO 03/02453. Such toothbrush includes a drive rocker coupled with a motor by a cam. The end of the drive rocker is fixedly mounted to the cam in a position eccentric to the motor shaft. As a result, when the motor shaft rotates the cam the drive rocker is moved in a funnel or cone-like manner. The drive rocker is mounted between the motor and the bristle support extending through a ring-shaped bearing element. By mounting the drive rocker between the motor and the bristle support with the bearing element, the drive rocker is fixed to a point so that the drive displacement of the drive rocker describes a double cone, wherein the peaks of the two converging cones lie in the area of the bearing element. The drive displacement of the drive rocker is transformed into the drive displacement of the bristle support.

It would be desirable to provide a drive system which imparts motions to a treating implement such as a power toothbrush wherein the motion is controlled in an effective, yet economical manner. It would also be desirable to provide such a drive system which could effectively operate using a small motor thereby having the treating implement be inexpensive and of small size without detracking from its efficiency.

SUMMARY OF INVENTION

An object of this invention is to provide a drive system for imparting motion to a treating implement such as a power toothbrush or the like so as to create and control the motion of the treating elements, such as the cleaning elements on the implement head.

A further object of this invention is to provide such a drive system which is effective in operation and yet economical in use and capable of being made in small size.

In accordance with this invention the drive system includes a cam rotatably driven around an axis of rotation by a motor. An outer surface of the cam has a closed loop cam track which is eccentric or offset to the axis of rotation. A control member is disposed between the cam and the treating implement head. The control member has a control slot extending completely through the control member with the slot being either symmetrical or being offset or non-symmetrical with respect to the axis of rotation of the motor. A pivot member is located between the control member and the treating implement head. A drive shaft has its drive end freely mounted in the cam track. The drive shaft extends through the control slot and through a hole in the pivot member with the driven end of the drive shaft mounted in a drive connection of the treating implement head. The drive shaft is located along an axis which differs from and is at an angle to the axis of rotation of the cam. During rotation of the cam, the drive shaft is confined in its path of motion by the control slot and cam track by permitting the drive shaft to travel freely in the cam track.

In a preferred practice of this invention the control slot is of straight linear shape extending radially with respect to the axis of rotation of the cam. The cam track is preferably circular in shape so that there is a uniform speed during rotation of the drive shaft. Alternatively, if the cam track is non-circular, such as being oval or elliptical, the speed of the linear reciprocating motion of the drive shaft can vary.

The drive system could be used in connection with various types of treating implements. In a preferred practice of the invention one such treating implement is a power toothbrush wherein at least a portion of the toothbrush head, which carries cleaning elements such as bristles, is oscillated back and forth along an arc in response to the arcuate reciprocating motion of the drive shaft. In a preferred practice of the invention where the control slot is of straight linear shape, the control slot is also parallel to the cleaning element carrying surface of the brush head. As a result, a planar motion is achieved in oscillating the brush head.

In an alternative embodiment, the control slot can be perpendicular to the cleaning element carrying surface which would create vertical movement. In a further alternative the cam track could be elliptical, rather than circular.

THE DRAWINGS

FIG. 1 is a front elevational view partly in section of a treating implement in the form of a power toothbrush in accordance with this invention;

FIG. 2 is a side elevational view partly in section of the treating implement shown in FIG. 1;

FIGS. 3-4 are cross-sectional views taken through FIG. 1 along the lines 3-3 and 4-4, respectively;

FIG. 5 is a cross-sectional view similar to FIG. 3 in a different phase of operation;

FIG. 6 is a cross-sectional view similar to FIG. 4 in a different phase of operation;

FIG. 7 is a schematic front elevational view showing one phase of operation of the drive system of this invention;

FIG. 7A is a view similar to FIGS. 3-4 combined in accordance with the phase of operation shown in FIG. 7;

FIG. 8 is a view similar to FIG. 7 in a different phase of operation;

FIG. 8A is a view similar to FIG. 7A in the phase of operation shown in FIG. 8;

FIG. 9 is a view similar to FIGS. 7-8 in a different phase of operation;

FIG. 9A is a view similar to FIGS. 7A and 8A in the phase of operation shown in FIG. 9;

FIG. 10 is a view similar to FIGS. 7, 8 and 9 in a different phase of operation;

FIG. 10A is a view similar to FIGS. 7A, 8A and 9A in the phase of operation shown in FIG. 10;

DETAILED DESCRIPTION

Figure 11:
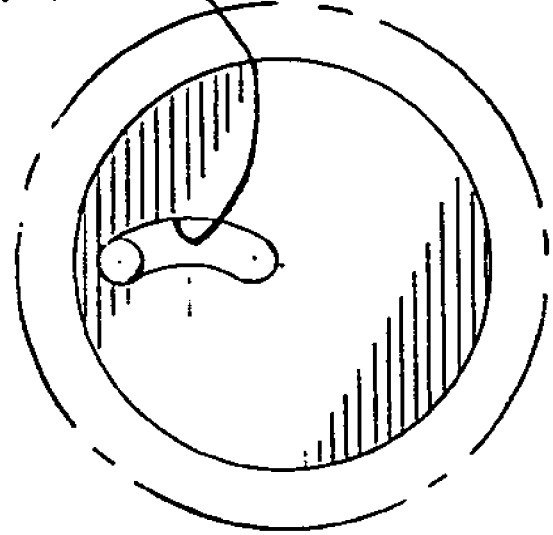
FIG. 11 is a view similar to FIG. 3 of a modified control member in accordance with this invention.

The present invention is directed to a drive system for imparting motion to a treating implement wherein a treating element(s) is movably mounted on the head of the implement. The invention may be practiced where the entire head is movable or where only a portion of the head is movable with that movable portion including at least some treating elements of the treating instrument. Representative examples of such treating implements include power toothbrushes, electric razors, clippers, massage devices and other personal grooming implements. It is to be understood that such listing of examples is not intended to limit the scope or practice of this invention.

One preferred practice of this invention is as a drive system for a power toothbrush. Such practice of the invention is illustrated in the drawings.

As shown in FIGS. 1-2 a power toothbrush 10 include a hollow handle 12 and a brush head 14 connected to the handle by a hollow neck 16. In the illustrated form of the invention the brush head 14 includes a fixed section 18 and a movable disk 20. Both fixed section 18 and disk 20 are provided with cleaning elements 21 extending outwardly from their outer surface 22. Such cleaning elements may take any suitable form such as bristles made of fibers of the like or elastomeric elements of any size or shape. Similarly, the disk 20 could be of any size or shape. For the sake of illustration disk 20 is shown as being of generally circular shape. Disk 20 is intended to be oscillated rotationally back and forth over a limited arc by the drive system generally indicated by the reference numeral 24.

The handle 12 of toothbrush 10 may be of generally known structure which includes a battery operated motor 26 having a motor shaft 28 which is rotated by the motor 26 when the toothbrush 10 is actuated in a known manner. The axis of rotation of shaft 28 is generally indicated by the reference numeral 30 in FIGS. 7-10.

In accordance with this invention the drive system 24 includes a cam 32 which is operatively connected to and rotated by motor shaft 28 in any suitable manner such as being mounted to the motor shaft 28 by the motor shaft extending into and being operatively connected to a collar 34 of the cam member. Cam may be of any suitable size and shape and preferably is in the form of a plate or disk which is relatively thin and is of circular shape having a diameter slightly less than the inner diameter of the portion of handle 12 in which cam 32 is located as best shown in FIGS. 1-2.

As illustrated in FIGS. 4 and 6 cam 32 includes a closed loop cam track 36 in its outer surface for reasons which will be later described.

Drive system 24 also includes a control member 38 located in the handle or neck of toothbrush 10 between cam 32 and head 14. Control member 38 may be of any suitable size and shape and preferably is a thin plate or disk which is mounted against shoulder 40 in handle 12. Control member 38 is illustrated as being circular in shape and mounted close to cam 32. Control member 38 could be of different shape and located further from cam 32. As illustrated in FIGS. 1-3 and 5 a control slot 42 extends completely through control member 38. Although cam member 32 is mounted for rotation, control member 38 has a fixed non-movable member mounting. Control slot 42 is positioned to be in line with the path of movement of cam track 36 while cam 32 is rotating, as later described. FIGS. 4 and 6 show the extreme different locations 180° apart of cam member 32 during its rotation. As shown therein in a preferred practice of this invention cam track 36 does not extend beyond the axis of rotation 30 or cam member center point, although cam track 36 is moved or rotates around the axis of rotation. Similarly, as shown in FIGS. 3 and 5 control slot 42 preferably does not extend beyond the axis of rotation, but could extend beyond the axis of rotation.

As later described control slot 42 may have various shapes and orientations. In a preferred practice of the invention the control slot 42 is of straight linear shape which is radially located with respect to the axis of rotation. Such radial location may begin at the axis of rotation 30. The invention, however, could be practiced where the control slot 42 is not confined solely to one side of the axis of rotation but could extend through and beyond the axis of rotation and could be symmetrical to the axis of rotation.

A further member of drive system 24 is a pivot member 44. Pivot member 44 is shown as being located in the neck 16 where the neck merges with head 14. Pivot member 44 could be of any size and shape such as a plate mounted at any suitable location or could be an inwardly extending shoulder. Pivot member 44 has a through hole 46 which is lined with a flexible bearing 48 similar to that described in U.S. Pat. No. 4,149,291, all of the details of which are incorporated herein by reference thereto. When such flexible bearing is made of a suitable elastomeric material it functions as a gasket.

A further element of drive system 24 is a drive shaft 50. Drive shaft 50 has a drive end 52 freely mounted in cam track 36. Drive shaft 50 extends through control slot 42 and through pivot member 44 with its driven end 54 extending into a slot 56 in the side of disk 20. The arrangement of a driven end in a disk to rotate in an oscillating manner the disk is similar to that of U.S. Pat. No. 5,625,914 and of WO 03/024353, all of the details of which are incorporated herein by reference. Preferably, the driven end 54 is of generally ball or spherical shape to minimize any slippage and provide a smooth operation as the driven end 54 reciprocates the disk 20 while driven end 54 is located in slot 56.

FIGS. 7-10A and also FIGS. 3-6 illustrate the manner of operation of drive system 24. FIGS. 7A-10A show the relationship between the control slot 42 and the cam track 36 with respect to drive shaft 50 by superimposing in phantom the control slot 42 against the cam member 32. Control slot is of a size only slightly larger than the diameter of shaft 50 so that shaft 50 snugly slides in slot 42.

FIGS. 7 and 7A illustrate the phase of operation where drive shaft 50 is located at the extreme outer end of control slot 42 and near the outer edge of cam 32 by being located in the portion of cam track 36 located near the edge of cam 32. This may be considered to 0° and 360° position. When in this position the movable disk 20 has been rotated to an angle of 15° of its axis of rotation. As cam 32 rotates cam track 36 is also rotated. During this rotation shaft 50 is confined by control slot 42 to slide in the control slot and yet still remain with its drive end in cam track 36. During this sliding motion drive shaft 50 pivots through pivot member 44 which in turn causes its driven end 54 to rotate disk 20. FIGS. 7-10A show the different locations at different phases of operation. FIG. 8 shows how the various members of drive system 24 have been moved when cam 32 has rotated 90° from the 0° or 360° position shown in FIG. 7. Thus, as shown in FIGS. 8 and 8A this 90° rotation causes drive shaft 50 to pivot so that the disk 20 is now moved to a location which is 7.04° off-center. As is clear from a comparison of FIGS. 7A and 8A, although cam 32 is rotating, drive shaft 50 is moved in a linear or planar direction because of the shape of control slot 42 which confines the moving drive shaft so that it can only move in the same straight linear shape of control slot 42. In the position shown in FIG. 8A drive shaft 50 has moved inwardly of control slot 42 as compared with its location shown in FIGS. 7 and 7A.

FIGS. 9 and 9A show the position of the various elements or members of drive system 24 when cam member 32 has been rotated 180° from that of FIG. 7. In this position, cam track 36 has also rotated 180° from the position it had in the phase shown in FIG. 7A. Drive shaft 50 has now moved to the inner end of control slot 42 so that the disk 20 has rotated 15° opposite to the position it had in FIG. 7. This thereby results in a 30° oscillation with 15° being on each side of the axis of rotation of disk 20.

FIG. 10 shows a further phase of operation as cam 32 continues to rotate back toward its original position. In the phase shown in FIGS. 10 and 10A there has been a 270° rotation. Cam track 36 has accordingly rotated 270° and drive shaft 50 is sliding back in control slot 42 toward its original position of FIGS. 7 and 7A.

By proper sizing and location of slot 42, pivot 44 and cam track 36, it is possible to control the degree of oscillation of disk 20. Preferably, the degree of oscillation should be 30° or less. The invention, however, might also be practiced where the degree of oscillation is in a range of 15° to 40°.

By providing a straight linear control slot the motion of drive shaft 50 is maintained planar. Where the straight linear control slot is parallel or is in the same plane as the outer surface 22 of head 14 carrying the cleaning members 21, the planar movement is also parallel to the outer surface 22. It is to be understood, however, that the invention could be practiced where other shapes and orientations of the control slot are used. Thus, for example, the control slot could be at a non-parallel angle such as an angle 90° to the outer surface 22 which would result in a planar movement that is not parallel to outer surface 22 as long as the control slot is of a straight linear shape. FIG. 11 illustrates a variation where the control slot 42A is of arcuate shape which would result in a corresponding upward/downward movement. Such arcuate movement, however, would be a reciprocating movement which would not result in a cone-like movement. Where a smooth arc is used for slot 42A the corresponding movement is also smooth.

Figure 12:
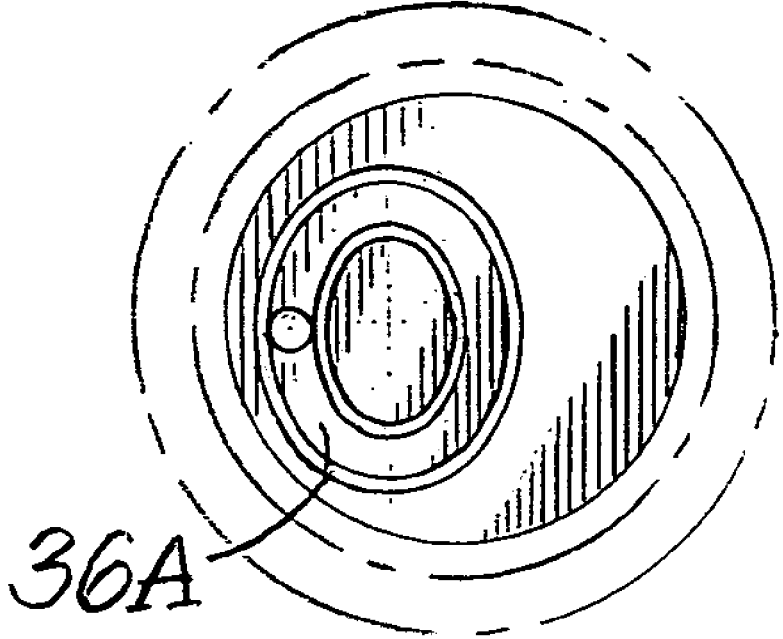
FIG. 12 is a view similar to FIG. 4 of a modified cam member in accordance with this invention.

In a preferred practice of the invention cam track 36 is a circular loop. Other shapes, however, may also be used. FIG. 12, for example, illustrates a cam track 36A which is somewhat oval or elliptical in shape. This form of cam track would result in a non-constant speed of movement of drive shaft 50. As illustrated in FIG. 12, the elliptical cam track 36A has a minor axis parallel to the outer surface 22 and of a diameter equal to that of circular cam track 36. The major axis of cam track 36A, is perpendicular to outer surface 22. Other forms of cam tracks can also be used.

In the preferred practice of the invention the cam track is a closed loop of smooth configuration. The invention, however, may be practiced where some irregular type closed loop is formed.

The location of pivot member 44 controls the torque and angle of oscillation resulting from the movement of drive shaft 50. By moving the pivot position closer to head 14 there would be an increase in torque, but there would also be a reduction in the angle of oscillation. Conversely, by moving the pivot position further from head 14 there would be a decrease in torque and an increase in the angle of oscillation.

Any suitable motor 26 may be used for rotating cam member 32. An example of a suitable motor is Mabuchi RF-N60CA-2050. Preferably, a motor with sufficient power yet relatively small in size would be used. As a result, it is possible to use a small diameter housing for handle 12 and small size components within the treating implement, such as toothbrush 10. This could be accomplished to thereby result in an inexpensive toothbrush or other treating implement which is of small size without sacrifice to the efficiency of operation.

In the illustrated practice of the invention wherein the treating implement is a toothbrush, the movable treating instrument, namely, the disk 20 on head 14 is reciprocated in an arcuate or rotational direction. Such arcuate movement is desirable to provide, for example, enhanced cleaning. Other forms of movement, however, may also be achieved such as a vibratory movement where the treating implement is intended to provide massage benefits.

In the illustrated version of the invention wherein there is planar reciprocating movement, the benefits achieved would be less wear on the various components such as the drive shaft and head as well as less vibration.

As can be appreciated the combination of a control member having a control slot which confines the direction of movement of the drive shaft and wherein the drive end of the drive shaft is freely mounted in a closed loop cam track offset or eccentric with regard to the axis of rotation of the cam member, there results an effective control in the movement of the drive shaft which can be transmitted to a portion of a head in a treating implement to thereby effectively control the movement of the treating elements such as the cleaning elements of a power toothbrush.

What is claimed is:

1. A drive system for imparting motion to a treating implement having a head, the head including a treating instrument that is separately moveable from the head and having implement elements, the drive system comprising:
   a motor, said motor having a rotatable motor shaft;
   a cam rotatably driven around an axis of rotation by said motor shaft said cam having an outer surface with a closed loop cam track having an inner wall and an outer wall and being eccentric to said axis of rotation;
   a treating implement head remote from said cam;
   a control member having a control slot extending completely therethrough;
   a pivot member located between said control member and said treating implement head, said pivot member having a through hole, said treatment implement head having a drive connection mounted to said treating implement and disposed toward said pivot member;
   a drive shaft having a longitudinal axis and a drive end and a driven end, the drive end and the driven end being coaxial along the longitudinal axis, said drive end being freely mounted and received in said cam track, said drive shaft extending through said control slot and through said hole in said pivot member, said driven end being operatively mounted to said drive connection of said implement head to cause said treating instrument to move, independently of the head, in response to movement of said drive shaft,
   said longitudinal axis of said drive shaft being different from and at an angle to said cam axis of rotation,
   said control slot controlling the path of movement of said drive shaft whereby rotation of said cam causes said drive end to slide along said inner wall and said outer wall of said cam track in response to the location of said drive shaft in said control slot with said drive shaft pivotally moving through said pivot member as said drive end slides along said inner wall and said outer wall of said cam track while said drive shaft slidably moves in said control slot to transmit the pivotal movement of said drive shaft to said drive end and to said drive connection for moving said treating instrument.

2. The drive system of claim 1 wherein said control slot is of straight linear shape to cause said drive shaft to move planarly.

3. The drive system of claim 2 wherein said cam track is circular.

4. The drive system of claim 2 wherein said cam track is non-circular.

5. The drive system of claim 4 wherein said cam track is oval.

6. The drive system of claim 2 wherein said control slot extends radially from said axis of rotation.

7. The drive system of claim 1 wherein said control slot is of non-straight linear shape.

8. The drive system of claim 7 wherein said control slot is of arcuate shape.

9. The drive system of claim 1 wherein said cam track does not extend beyond said axis of rotation.

10. The drive system of claim 1 wherein said drive connection includes a slot in a portion of said treating implement head, and said driven end of said drive shaft terminates in a ball mounted in said implement head slot.

11. The drive system of claim 1 wherein said drive shaft extends through a flexible bearing in said through hole of said pivot member.

12. The drive system of claim 1 wherein said treating implement is a toothbrush, said head being a cleaning head having an outer surface, said treating elements being cleaning elements extending outwardly from said outer surface and located on at least a portion of said head, and said drive connection being a slot in said portion of said head.

13. The drive system of claim 12 wherein said control slot is of straight linear shape parallel to said outer surface of said head.

14. The drive system of claim 13 wherein said cam track is circular.

15. The drive system of claim 14 wherein said pivot member is a thin plate, and said control member is a thin disk.

16. The drive system of claim 15 wherein said control slot extends radially from said axis of rotation, and said cam track does not extend beyond said axis of rotation.

17. The drive system of claim 16 wherein said treating instrument is oscillated back and forth over a range no greater than 30 degrees.

18. The drive system of claim 12 is of straight linear shape at an angle which is non-parallel to said outer surface of said head.

19. A drive system for imparting motion to a treating instrument on a treating implement, comprising:

a head having the treating instrument rotatably mounted thereon, wherein the treating instrument moves independently of the head;

a plurality of implement elements mounted to the treating element;

a motor having a rotatable motor shaft, a cam rotatably driven around an axis of rotation by said motor shaft, said cam having an outer surface with a closed loop cam track having an inner wall and an outer wall and being eccentric to said axis of rotation;

a control member having a control slot extending completely therethrough;

a pivot member located between said control member and said head, said pivot member having a through hole, wherein said head has a drive connection mounted to said treating instrument and disposed toward said pivot member;

a drive shaft having a longitudinal axis and a drive end and a driven end, the drive end and the driven end being coaxial along the longitudinal axis, said drive end being freely mounted and received in said cam track, said driven end being operatively mounted to said drive connection of said head to cause said treating instrument to move in response to movement of said drive shaft, said longitudinal axis of said drive shaft being different from and at an angle to said cam axis of rotation, said control slot controlling the path of movement of said drive shaft whereby rotation of said cam causes said drive end to slide along said cam track in response to the location of said drive shaft in said control slot with said drive shaft pivotally moving through said pivot member as said drive end slides along said inner wall and said outer wall of said cam track while said drive shaft slidably moves in said control slot to transmit the pivotal movement of said drive shaft to said drive end and to said drive connection for moving at least a portion of said treating instrument.

20. The drive system of claim 19, wherein the movement of the treating instrument is an oscillatory, rotational movement.

* * * * *